US012605087B2

(12) United States Patent
Polert et al.

(10) Patent No.: US 12,605,087 B2
(45) Date of Patent: Apr. 21, 2026

(54) METHOD AND DEVICE FOR MEASURING THE CONTENT OF AT LEAST ONE GAS IN EXHALED AIR

(71) Applicant: WEINMANN EMERGENCY MEDICAL TECHNOLOGY GMBH + CO. KG, Hamburg (DE)

(72) Inventors: Annika Polert, Norderstedt (DE); Johannes Kreuzer, Hamburg (DE); Christian Neuhaus, Quickborn (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 484 days.

(21) Appl. No.: 18/025,025

(22) PCT Filed: May 26, 2021

(86) PCT No.: PCT/DE2021/100455
§ 371 (c)(1),
(2) Date: Mar. 7, 2023

(87) PCT Pub. No.: WO2022/053094
PCT Pub. Date: Mar. 17, 2022

(65) Prior Publication Data
US 2023/0329579 A1      Oct. 19, 2023

(30) Foreign Application Priority Data
Sep. 10, 2020      (DE) ..................... 10 2020 123 623.9

(51) Int. Cl.
A61B 5/083      (2006.01)
A61B 5/097      (2006.01)
A61M 16/08      (2006.01)

(52) U.S. Cl.
CPC .......... *A61B 5/0836* (2013.01); *A61B 5/0833* (2013.01); *A61B 5/097* (2013.01); *A61M 16/085* (2014.02); *A61M 2230/43* (2013.01)

(58) Field of Classification Search
None
See application file for complete search history.

(56) References Cited

U.S. PATENT DOCUMENTS

| | | |
|---|---|---|
| 8,342,178 B2 | 1/2013 | Hengstenberg |
| 2006/0201507 A1 | 9/2006 | Breen |

(Continued)

FOREIGN PATENT DOCUMENTS

DE      102008022761 A1      11/2009

OTHER PUBLICATIONS

International Search Report Dated Sep. 7, 2021, PCT/DE2021/100455, 2 Pages.

*Primary Examiner* — Jay B Shah
(74) *Attorney, Agent, or Firm* — LUCAS & MERCANTI, LLP; Klaus P. Stoffel

(57) ABSTRACT

A method and a device for measuring the content of at least one gas in exhaled air and to a device for ventilation. Due to the combination of a rapid respiratory phase sensor with a valve controllable depending on the detected respiratory phase, the use is made possible of a slower gas sensor to measure the content of a specific gas in the exhaled air during a certain period in the respiratory cycle so that the use of more economical and/or smaller and/or more accurate gas sensors is possible.

11 Claims, 5 Drawing Sheets

(56)     References Cited

U.S. PATENT DOCUMENTS

| 2013/0165806 | A1  |      | 6/2013  | Wondka |             |
|--------------|-----|------|---------|--------|-------------|
| 2015/0265184 | A1  | *    | 9/2015  | Wondka | A61B 5/082  |
|              |     |      |         |        | 600/532     |
| 2015/0335267 | A1  | *    | 11/2015 | Cormier | A61B 5/0836 |
|              |     |      |         |        | 600/532     |

* cited by examiner

METHOD AND DEVICE FOR MEASURING THE CONTENT OF AT LEAST ONE GAS IN EXHALED AIR

CROSS-REFERENCE TO RELATED APPLICATIONS

The present application is a 371 of International application PCT/DE2021/100455, filed May 26, 2021, which claims priority of DE 10 2020 123 623.9, filed Sep. 10, 2020, the priority of these applications is hereby claimed and these applications are incorporated herein by reference.

BACKGROUND OF THE INVENTION

The invention relates to a device for measuring the content of at least one gas in exhaled air especially for use with a ventilator.

The invention further relates to a method for measuring the content of at least one gas in exhaled air.

The invention further relates to a device for ventilation in the sense of a ventilator, especially an emergency ventilator, comprising a device for measuring the content of at least one gas in exhaled air.

When ventilating patients with air by at least semimanual ventilation or by automatic ventilation, it is of interest to determine various gas contents both in the air supplied to the patient and in the exhaled air.

For example, the content of carbon dioxide ($CO_2$) or content of oxygen ($O_2$) is determined using suitable sensors.

Depending on the application, the respective gas must be measured with high temporal resolution.

The respiratory cycle of a human and of other living beings with corresponding breathing is composed of inhalation (inspiration) and exhalation (expiration). When ambient air is inhaled, the inspiratory oxygen concentration ($FiO_2$) is about 20.9% by volume. At the end of exhalation, what remains after the gas exchange between the lungs and cardiovascular system is an end-tidal oxygen concentration ($etO_2$) of about 16% by volume in the exhaled air. Upon inhalation, the $CO_2$ content ($FiCO_2$) of the respiratory gas is about 0% by volume (0.04% by volume $CO_2$ in the ambient air), whereas it rises distinctly upon exhalation, such that an end-tidal $CO_2$ concentration ($etCO_2$) of approx. 4.5% by volume is measurable.

In medicine, it is for example customary to determine the course of the $CO_2$ content in the exhaled air during the respiration of a patient. At the end of exhalation, the end-tidal $CO_2$ concentration ($etCO_2$) is determinable, provided that the $CO_2$ sensor technology used is appropriately rapid and thus of appropriately high temporal resolution. The concentration plateau at the end of exhalation is determinable as a result.

For measurement of the $CO_2$ content in the respiratory air, there are basically two methods in the prior art that are used in connection with the ventilation of patients. Depending on the respiratory phase, the respiratory gas flows toward the patient or away from said patient through a hose system of the device for ventilation. In a main-stream method, the total respiratory gas of the patient is directly analyzed in or at said hose system and thus in the main stream of the respiratory gas, whereas, in a secondary-stream method, a sample gas is sucked from the main stream and analyzed. The sample gas is generally sucked close to the patient, so that both the inhaled gas and the exhaled gas can be analyzed.

For measurement of the $CO_2$ content in the respiratory air, what is typically present in the ventilator is a measurement cuvette, in which the sample gas is transilluminated with near-infrared light. The $CO_2$ in the sample gas absorbs some of the light, and so the $CO_2$ content in the respiratory air is determinable from the remaining light intensity. This sensor technology is comparatively rapid, meaning that the $CO_2$ concentration in the respiratory air is exactly determinable over the entire respiratory cycle (the rise time $t(10\%\text{-}90\%)$ of such $CO_2$ sensors is about 90 ms).

For measurement of the $O_2$ content in the respiratory air, there are basically various sensor technologies, for example paramagnetic sensors, galvanic cells, zirconium dioxide sensors, fluorescence sensors and laser spectroscopy. The various sensors additionally differ in terms of their size, response time, measurement accuracy, availability, service life and cost, with faster sensors usually being more expensive than slower sensors.

Relatively small and advantageous sensors for measuring the $O_2$ content are, for example, galvanic oxygen sensors, in which the gas reaches the cathode across a thin membrane and a first reaction takes place at said cathode. Via the liquid electrolyte of the sensor, the resultant charge carriers reach the cathode, where a further reaction takes place. At the same time, the coating of the anode is worn away with each reaction, which is why the sensor is also referred to as a consuming sensor. The resultant current is proportional to the $O_2$ concentration in the sample gas, but also dependent on the pressure and the temperature. Such galvanic $O_2$ sensors do not require an external energy source, but are only usable for one to two years, depending on the use and response time of the sensor. The rise time $t(10\%\text{-}90\%)$ of such sensors is typically about 2 s, meaning that $O_2$ content measurement with high temporal resolution is not a possible use.

For measurement of the $O_2$ content in the respiratory air, the use of fast $O_2$ sensors especially in emergency ventilation is not customary for space and/or cost reasons. Nevertheless, it is of great interest to medical personnel to determine the end-tidal oxygen concentration ($etO_2$) in order to be able to draw conclusions about the amount of the oxygen taken up by a patient during the ventilation of said patient and the amount of the oxygen not taken up by said patient and thus exhaled.

Especially with preoxygenation, a procedure in which nitrogen is washed out of the lungs of a patient and replaced with oxygen, the $etO_2$ value plays an important role. With the aid of the $etO_2$ value, the end time point of the procedure can be determined from measured data, and so it does not have to be inferred from experience, which may be inaccurate for the individual patient.

Determining the content of other gases in the respiratory air, for example VOCs (volatile organic compounds), hydrogen or anesthetic gases, is also of interest in certain applications.

SUMMARY OF THE INVENTION

It is therefore an object of the invention to provide an improved device for measuring the content of at least one gas in exhaled air.

It is a further object of the invention to provide a device for measuring the content of at least one gas in exhaled air that allows the determination of the content of said gas in a manner sufficient for the particular application, even with a sensor having a slow response time.

It is a further object of the invention to provide an improved device for ventilation.

It is a further object of the invention to provide a method for measuring the content of at least one gas in exhaled air that allows the determination of the content of said gas in a manner sufficient for the particular application, even with a sensor having a slow response time.

The below-disclosed features of a device for measuring the content of at least one gas in exhaled air are part of the invention, both individually and in all implementable combinations.

A device for measuring the content of at least one gas in exhaled air, which device is according to the invention, comprises at least one device for determining the respiratory phase and additionally at least one gas sensor, and also at least one control unit and at least one controllable valve and/or one pump device.

The device for determining the respiratory phase is designed, in an advantageous embodiment of the invention, for determination of the current respiratory phase and, in particularly advantageous embodiments of the invention, for detection of a defined region in the respiratory cycle of a patient. To this end, the device for determining the respiratory phase comprises at least one suitable respiratory phase sensor.

In one embodiment of the invention, the device for determining the respiratory phase comprises at least one respiratory phase sensor designed as a CO2 sensor, an O2 sensor, a humidity sensor, a temperature sensor, a pressure sensor or a flow sensor.

The at least one respiratory phase sensor of the device for determining the respiratory phase is arranged for measurement by a secondary-stream method or a main-stream method based on the main stream of the respiratory air.

In a preferred embodiment of the invention, if a pressure sensor or a flow sensor is used in the device for determining the respiratory phase, the respective respiratory phase sensor is arranged for measurement in a main-stream method. The use of CO2, temperature or humidity sensors is also possible for main-stream measurement.

The volumetric flow rate of the respiratory air toward the patient lies in an order of magnitude of about 0 to 100 l/min. In embodiments of the invention, the suction of sample gas for a measurement in a secondary-stream method is about 100 ml/min.

In a preferred embodiment of the invention, if a CO2 sensor, an O2 sensor, a humidity sensor or a temperature sensor is used as a respiratory phase sensor in the device for determining the respiratory phase, the respective respiratory phase sensor is arranged for measurement in a secondary-stream method.

In an advantageous embodiment of the invention, the device for measuring the content of at least one gas in exhaled air comprises at least one water filter or other mechanism for drying the sample gas, so that, in the region of the measurement mechanism, condensation of the water vapor generally present especially in the exhaled air is avoided, as is an associated impairment of the measurements. In particular, the use of at least one water filter or one mechanism for drying the sample gas is advantageous in the case of secondary-stream measurement. A humidity measurement after the sample gas has been dried is, of course, not very helpful for determining the respiratory phase.

As already described above, the concentration of CO2 and O2 changes in the course of the respiratory cycle. The humidity and temperature and the pressure and flow of the respiratory air are also dependent on the respiratory cycle. For instance, the exhaled air is generally more humid and warmer than the air supplied to the patient; moreover, it flows in the opposite direction.

With the aid of a device for determining the respiratory phase according to the present invention, at least one of the aforementioned measurement values is measurable with the aid of an appropriate respiratory phase sensor having high temporal resolution (fast sensor), and the course of measurement values is evaluable as regards to which respiratory phase of the respiratory cycle the respiration or ventilation of a patient is currently in.

Besides the inspiration phase and the expiration phase as such, what is especially of interest is the detection of the end-tidal region at the end of the expiration phase.

In a particularly advantageous embodiment of the invention, the device for determining the respiratory phase is therefore designed for detection of the end-tidal region.

With the aid of the control unit, the at least one controllable valve and/or the pump device is actuable according to the detected respiratory phase.

In an advantageous embodiment of the invention, the at least one controllable valve comprises at least one openable and closable valve path, via which the gas to be measured is suppliable to at least one gas sensor.

Alternatively or additionally, the pump device is actuable with the aid of the control unit in such a way that the gas to be measured is suppliable to at least one gas sensor.

In a particularly preferred embodiment of the invention, the device for determining the respiratory phase is designed for determination of the end-tidal region and the controllable valve is actuable with the aid of the control unit such that the at least one valve path of the controllable valve is open for the duration of the end-tidal region of the expiration phase and is closed when the inspiration phase starts, so that the gas sample of the respiratory air that has been supplied into the region of the at least one gas sensor comes from the end-tidal region of the expiration phase.

Correspondingly, the above-described logic is possible, according to the invention, in relation to opening or closing one or more valve paths of the controllable valve according to any desired regions (respiratory phases) in the respiratory cycle.

In preferred embodiments of the invention, the device for determining the respiratory phase is designed for determination of the end-tidal region and the pump device is actuable with the aid of the control unit such that the pump device conveys sample gas into the region of the gas sensor for the duration of the end-tidal region of the expiration phase and switches off when the inspiration phase starts, so that the gas sample of the respiratory air that has been supplied into the region of the at least one gas sensor comes from the end-tidal region of the expiration phase.

The above-described construction of a device for measuring the content of at least one gas in exhaled air, which device is according to the invention, thus allows the specific supply of a sample of the respiratory air from a defined respiratory phase and subsequently a relatively long period of time in which the respiratory air sample is measurable with the aid of the at least one gas sensor for determining the content of at least one gas in the respiratory air. The use of gas sensors having a longer rise time and/or a higher degree of accuracy is possible as a result (slow sensor).

In a particularly preferred embodiment of the invention, at least one gas sensor is designed as an O2 sensor, so that the end-tidal O2 content of the respiratory air (etO2 value) is determinable.

The frequency of the respiratory cycle is typically 10/min in adults and 40/min in children and can be up to 110/min in the context of cardiopulmonary resuscitation. Accordingly, the period of the respiratory cycle is about between 540 ms (cardiopulmonary resuscitation) and 6 s (typical respiratory cycle of an adult).

The quantity of measurement values required for reliable determination of the respiratory phase depends on the length of the region of interest. Depending on the frequency or period of the desired ventilation mode (e.g., adult, child, cardiopulmonary resuscitation), the maximum permissible rise time for a gas sensor is thus determinable.

In one embodiment of the invention, the maximum permissible rise time for a fast sensor for respiratory phase detection is determinable as $t_{10-90}=60/(10 \cdot f_{max})$, with 10 measurement values per breath being assumed and $f_{max}$ specifying the maximum frequency of the respiration or ventilation to be expected in 1/min. Thus, ventilation of a "giant" with an expected frequency $f_{max}$ of 5/min means a maximum rise time $t_{10-90}$ of 1200 ms, ventilation for an adult with an expected frequency $f_{max}$ of 10/min means a maximum rise time $t_{10-90}$ of 600 ms, ventilation for a child with an expected frequency $f_{max}$ of 20/min means a maximum rise time $t_{10-90}$ of 300 ms, ventilation for an infant with an expected frequency $f_{max}$ of 50/min means a maximum rise time $t_{10-90}$ of 120 ms, ventilation for resuscitation with cardiac massage with an expected frequency $f_{max}$ of 100/min means a maximum rise time $t_{10-90}$ of 60 ms, and ventilation with a somewhat too rapid cardiac massage with an expected frequency $f_{max}$ of 110/min means a maximum rise time $t_{10-90}$ of 54.5 ms.

A sensor with high temporal resolution, or fast sensor, in the context of this application is thus, based on the respiration or ventilation of an adult, a sensor having a rise time in a range less than about 500 ms and a sensor having a longer rise time, or slow sensor, in the context of this application has a rise time of greater than about 500 ms.

In an advantageous embodiment of the invention, a fast sensor having a rise time of at most 90 ms is used for respiratory phase detection.

In a particularly advantageous embodiment of the invention, a fast sensor having a rise time of at most 60 ms is used for respiratory phase detection.

If the device for measuring the content of at least one gas in exhaled air, which device is according to the invention, is designed for measurement, according to a secondary-stream method, of at least one of the measurement values measurable with the aid of the device for determining the respiratory phase or with the aid of the further gas sensor, it preferably comprises a pump device, by means of which a gas sample is pumpable out of the main stream and transportable into the region of the respective sensor.

In one embodiment of the invention, the pump device is designed as a suction pump.

In a particularly preferred embodiment of the invention, the device for measuring the content of at least one gas in exhaled air is additionally designed for measurement of the content of at least one gas in the inhaled air.

To this end, the device for measuring the content of at least one gas in exhaled air comprises a further controllable valve, or the controllable valve is designed as a multiport valve, the multiport valves being openable or closable in line with defined respiratory phases with the aid of the device for determining the respiratory phase and the aid of the control unit.

In one embodiment of the invention, the device for measuring the content of at least one gas in exhaled air is designed for inspiratory oxygen measurement.

In a particularly preferred embodiment of the invention, what is used for determination of the inspiratory oxygen content is the same sensor that is also used for determination of the end-tidal oxygen content.

Since the composition of the air used for ventilation is generally subject to only slight fluctuations, the oxygen content (or the content of another gas of interest) of the air supplied to a patient is suppliable to the O2 sensor (or another gas sensor measuring the content of the gas of interest) in the period of the respiratory cycle that is not required for determination of the etO2 value (or the content of the other gas of interest in the respiratory phase of interest), and so the content of the respective gas in the respiratory air supplied to the patient and in the exhaled air is determinable by means of the gas sensor in an alternating manner.

A device for ventilation according to the invention comprises at least one device for measuring the content of at least one gas in exhaled air, which device is according to the invention, as per the foregoing description.

The below-disclosed features of a method for measuring the content of at least one gas in exhaled air are part of the invention, both individually and in all implementable combinations.

A method for measuring the content of at least one gas in exhaled air, which method is according to the invention, comprises at least the following method steps:

1. determining the respiratory phase
2. detecting whether there is a predetermined respiratory phase in a respiratory cycle
3. supplying a gas sample to at least one gas sensor
4. isolating the gas sample in the region of the at least one gas sensor
5. measuring the supplied gas sample with the aid of the at least one gas sensor
6. terminating the isolation of the gas sample In advantageous embodiments, the aforementioned method steps proceed sequentially and continuously in a loop until the measurement has ended.

In a particularly preferred embodiment of the method according to the invention, the determination of the respiratory phase is carried out continuously and in parallel to the other method steps In embodiments of the invention of the method, the supplying of the gas sample to the at least one gas sensor is carried out possibly continuously and independently of the respiratory phase until the gas sample has been isolated, i.e., this step can also be carried out before the detection of the at least one predetermined respiratory phase and possibly also before the (first) determination of the respiratory phase.

In a preferred embodiment of the invention, the determination of the respiratory phase is carried out by the continuous evaluation of successively measured measurement values of at least one sensor of a device for determining the respiratory phase, use being made of at least one sensor for measurement of the CO2 content, the O2 content, the humidity, the temperature, the pressure and/or the flow of the respiratory gas, especially the exhaled air, with high temporal resolution.

In embodiments of the method, the determination of the respiratory phase is carried out by main-stream measurements.

In other embodiments of the method according to the invention, the determination of the respiratory phase is carried out by secondary-stream measurements.

In embodiments of the method, the respective respiratory phase is detected by the measurement values lying above or below a specified threshold value or multiple specified threshold values.

For various measurement values, threshold values for detecting the respiratory phase are specified below by way of example.

In one embodiment of the invention, if a CO2 sensor is used for determination of the respiratory phase, a value for CO2>2.5% by volume indicates the expiration phase. Said value is typically 5% by volume during expiration. When the value subsequently falls below 0.5% by volume CO2 again, an inspiration phase is detected.

In another embodiment of the invention, the threshold value of the CO2 content in the respiratory air for determining the inspiration phase is set to about 0.8 CO2max and thus to about 3.6% by volume CO2. This allows faster detection of the inspiration phase than a threshold at 0.5% by volume CO2, but, depending on the CO2 contents of the respiratory air that are actually achieved when ventilating the patient, may hide problems with the robustness of respiratory phase detection.

In one embodiment of the invention, if an O2 sensor is used for respiratory phase detection, then when ventilating a patient with room air, a value for O2>20% by volume indicates an inspiration phase and a value for O2<19% indicates an expiration phase.

In one embodiment of the invention, if an O2 sensor is used for respiratory phase detection, then when ventilating a patient with pure oxygen, a value for O2>98% indicates an inspiration phase and a value for O2<98% by volume indicates an expiration phase.

In one embodiment of the invention, if a main-stream flow sensor is used for respiratory phase detection, a value for the flow >0.5 l/min (in the patient's direction) indicates an inspiration phase and a value for the flow <−0.5 l/min (coming from the patient) indicates an expiration phase.

In one embodiment of the invention, if a main-stream gas temperature sensor is used for respiratory phase detection, a value for the temperature T>32° C. indicates an expiration phase and a value for the temperature T<28° C. indicates an inspiration phase.

In one embodiment of the invention, if a humidity sensor for measuring relative humidity (rH) is used for respiratory phase detection, a value for rH>90% indicates an expiration phase, since humid gas is being exhaled, and a value for rH<85% indicates an inspiration phase.

In other embodiments of the invention, the respiratory phase is detected by a comparison with previously measured measurement values of at least one respiratory cycle, preferably multiple respiratory cycles.

In embodiments of the invention, the respiratory phase is detected with the aid of dynamically adjustable threshold values, said threshold values being adapted on the basis of at least one measured parameter.

In embodiments according to the invention, the use of algorithms, for example fuzzy logic, is also conceivable for detection of the respiratory phase. Other embodiments utilize the first or the second derivative of the particular measurement value signals considered, for detection of the respiratory phase.

In any case, the isolation of the gas sample in the region of the at least one gas sensor according to the respiratory phase only occurs when a defined respiratory phase (e.g., the end-tidal region) has been detected.

In advantageous embodiments, the end-tidal region is detected by the use of a delay after the detection of the end of the expiration phase or the start of the inspiration phase. The end-tidal region is the region about 200 ms to 50 ms before the end of the expiration phase, and so the respiratory gas from the end-tidal region in the expiration phase is isolated in the region of the gas sensor by appropriate actuation of the controllable valve and/or the pump device.

In a preferred embodiment of the invention, the sample gas from the last 30% of the expiration phase is conducted into the region of the gas sensor for isolation.

The termination of the isolation of the gas sample in the region of the at least one gas sensor occurs once the measurement of the content of the gas of interest in the gas sample has been completed and/or once a specified time has elapsed and/or once this is specified by an external signal.

In one embodiment of the method according to the invention, the isolation of the gas sample in the region of the at least one gas sensor is carried out by closing at least one valve path of a controllable valve and/or by switching off the pump device. In this embodiment, the termination of the isolation of the gas sample in the region of the at least one gas sensor is carried out by opening the at least one valve path of the controllable valve and/or switching on the pump device.

In embodiments of the invention, the supplying of the respiratory gas to be analyzed into the region of the gas sensor is, with the exception of the isolation phase, carried out continuously or specifically immediately before the isolation phase, and so it is ensured that respiratory gas from the respiratory phase of interest is present in the region of the at least one gas sensor during the isolation phase.

A dead volume possibly present in a conduit system should be noted when specifically supplying the respiratory gas immediately before the isolation phase and, in such embodiments of the method, is accordingly discharged from the region of the at least one gas sensor before the isolation phase. For example, this is realized by waiting for a pre-defined period (delay) after the detection of the relevant respiratory phase, which can be chosen according to the flow rate of the sample gas or the pump output of the pump device, and the conduit volume of the line guiding the sample gas, and the geometry of the measurement device.

In embodiments of the method according to the invention, the detection of the respiratory phase and the isolation of the gas sample is not carried out in each respiratory cycle, but is carried out regularly, for example in every xth respiratory cycle ($x \in N$, $x \neq 1$).

In this case, in preferred embodiments of the method, the respectively isolated gas sample is measured and a moving average is formed over the measurement values of the individual recorded breaths.

In a preferred embodiment, the method according to the invention is designed for determination of the end-tidal O2 content (etO2 value) in the respiratory air.

With the aid of the device for measuring the content of at least one gas in exhaled air, which device is according to the invention, and the method for measuring the content of at least one gas in exhaled air, which method is according to the invention, and a device for ventilation according to the invention, what is therefore made possible by the combination of a fast respiratory phase sensor with a valve controllable according to the detected respiratory phase is the use of a slower gas sensor for measuring the content of a particular gas in the respiratory air during a particular time segment in the respiratory cycle, and so the use of gas sensors which are more cost-effective and/or smaller and/or more accurate is made possible.

BRIEF DESCRIPTION OF THE DRAWING

The figures described hereinbelow depict exemplary embodiments of the invention, where.

DETAILED DESCRIPTION OF THE INVENTION

Figure 1:
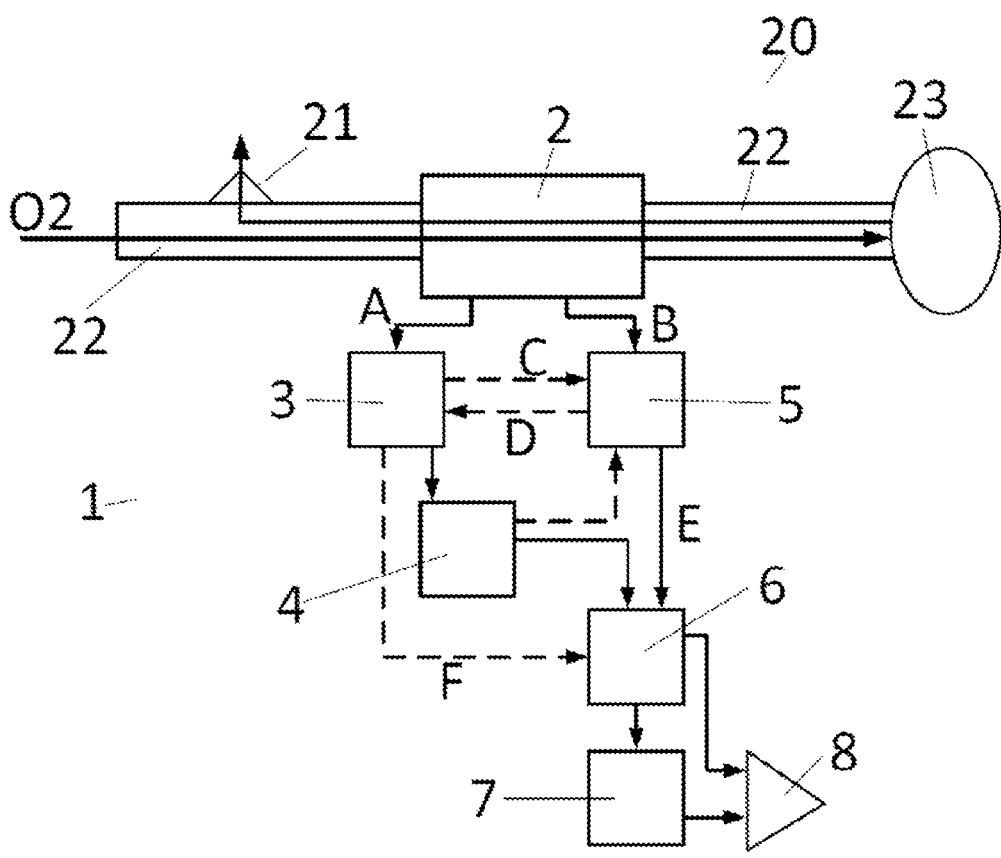
FIG. 1: shows a schematic block diagram of a device for measuring the content of at least one gas in exhaled air, which device is according to the invention.

FIG. 1 depicts a schematic block diagram of one embodiment of the invention of a device for measuring the content of at least one gas in exhaled air (1) in the region of a partially shown device for ventilation (20).

The device for measuring the content of at least one gas in exhaled air (1) is connected near a patient to the respiratory air stream of the device for ventilation (20) via a connection mechanism (2).

In the embodiment depicted, the connection mechanism (2) is designed as part of the respiratory air line (22) and arranged between the patient valve (21) and the mask (23) of the device for ventilation (20), so that the respiratory air conducted toward the mask (23) or toward a patient in the inspiration phase flows through the connection mechanism (2) just like the respiratory air conducted in the expiration phase from the mask (23) or from the patient toward the patient valve (21).

The respiratory air conducted from the device for ventilation (20) through the respiratory air line (22) for ventilation of a patient is identified by O2 in the illustration and includes both the use of ambient air for ventilation and the use of oxygen-enriched air.

The device for measuring the content of at least one gas in exhaled air (1) further comprises a device for determining the respiratory phase (3), which is connected to the connection mechanism (2). Embodiments according to the invention include both arrangements which realize a measurement in a main-stream method and arrangements which realize a measurement in a secondary-stream method.

Furthermore, the embodiment shown of a device for measuring the content of at least one gas in exhaled air (1) comprises a controller (4), a pump device (5), a controllable valve (6), a gas sensor (7) and an outlet (8).

With the aid of the pump device (5), a gas sample is pumpable out of the respiratory air stream in the region of the connection mechanism (2).

With the aid of the controller (4), at least the controllable valve (6) is actuable according to the respiratory phase determined with the aid of the device for determining the respiratory phase (3), so that the gas sample conveyed with the aid of the pump device (5) is conductable through an opened valve path toward the gas sensor (7) or directly conductable toward the outlet (8).

The dashed arrows show optional configurations of a device for measuring the content of at least one gas in exhaled air (1), which device is according to the invention and which configurations will be explained hereinbelow.

In a first modification of the invention of the embodiment shown in FIG. 1 of a device for measuring the content of at least one gas in exhaled air (1), the pump device (5) is connected to the device for determining the respiratory phase (3) and to the connection mechanism (2) such that gas samples conveyed with the aid of the pump device (5) also always flow through the device for determining the respiratory phase (3).

In this case, the pump device (5) is arranged, in the flow direction of the gas samples, either upstream (flow direction along arrows B, D, F) or downstream (flow direction along arrows A, C, E) of the device for determining the respiratory phase (3).

Also conceivable in modifications of the invention is an arrangement of the pump device (5) between the controllable valve (6) and the gas sensor (7) or between the gas sensor (7) and the outlet (8).

In one embodiment of the invention, the pump device (5) is also actuable with the aid of the control unit (4) according to the respiratory phase.

In a further embodiment of the invention, the device for measuring the content of at least one gas in exhaled air (1) does not comprise a controllable vale (6) and, instead, only comprises at least one pump device (5) which is actuable with the aid of the control unit (4) according to the respiratory phase and by means of which a gas sample is conductable into the region of the gas sensor (7) and isolatable in the region of the gas sensor (7) according to the respiratory phase.

Figure 2:
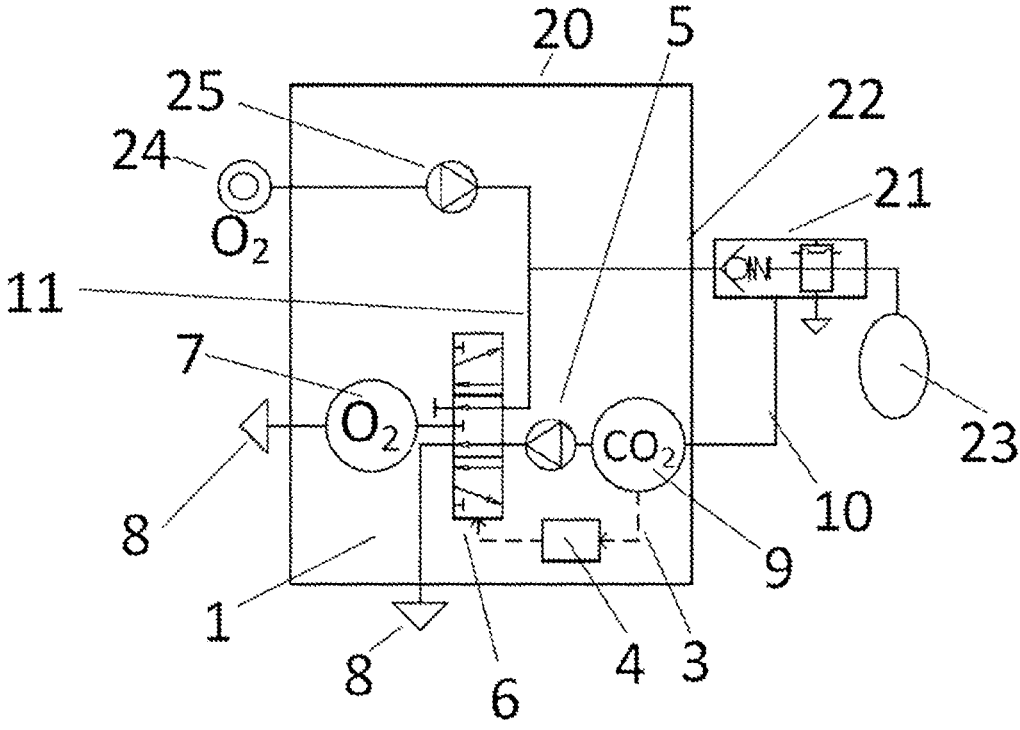
FIG. 2: shows a further schematic block diagram of one embodiment of a device for measuring the content of at least one gas in exhaled air, which device is according to the invention, containing further details.

FIG. 2 shows a block diagram of a further embodiment of the invention of a device for measuring the content of at least one gas in exhaled air (1) or of a device for ventilation (20) according to the invention.

The device for measuring the content of at least one gas in exhaled air (1) is at least partially integrated into the housing of the device for ventilation (20).

Arranged in the region of the patient valve (21) is the connection device (2) (not depicted), which is connected via a withdrawal line (10) to a respiratory phase sensor (9) of the device for determining the respiratory phase (3), which respiratory phase sensor (9) is designed as a CO2 sensor and has high temporal resolution. Arranged downstream of the respiratory phase sensor (9) is the pump device (5), so that respiratory gas samples are always conducted through the respiratory phase sensor (9). Arranged downstream of the pump device (5) is the controllable valve (6), which is designed as a multiport valve and comprises two input ports and three output ports in the embodiment shown. Connected to the first input port is the pump device (5), so that a gas sample is pumpable by means thereof through the first input port into the controllable valve (6). Connected to the second input port is a branch (11) of the respiratory air line (22) that is arranged upstream of the patient valve (21) in the flow direction of the respiratory air toward the patient, so that said branch (11) always guides only the respiratory air used for ventilation and not the exhaled air. The first output port of the controllable valve (6) is a dead end (tightly sealed), what is connected to the second output port is the gas sensor (7), and what follows the third output port is the outlet (8).

With the aid of the control unit (4), the controllable valve (6) is switchable according to the respiratory phase in such a way that the gas samples are successively conductable from the region of the connection device (2) and from the branch (11) of the respiratory air line (22) toward the gas sensor (7) or directly toward the outlet (8).

In the embodiment of the invention that is depicted, the gas sensor (7) is designed as an O2 sensor, so that the O2 content of the respiratory air guided toward the patient or the O2 content of the exhaled air of the patient is measurable depending on the valve status of the controllable valve (6).

The device for ventilation (20) further comprises a respiratory air source (24), which optionally comprises an oxygen source for enriching the respiratory air with oxygen, and a fan or valve (25), by means of which the respiratory air is actively conveyable (fan) or the flow of the respiratory air is controllable (valve).

Furthermore, the device for ventilation (20) comprises a mask (23), which is fittable on the face of a patient for ventilation of the patient.

Figure 3:
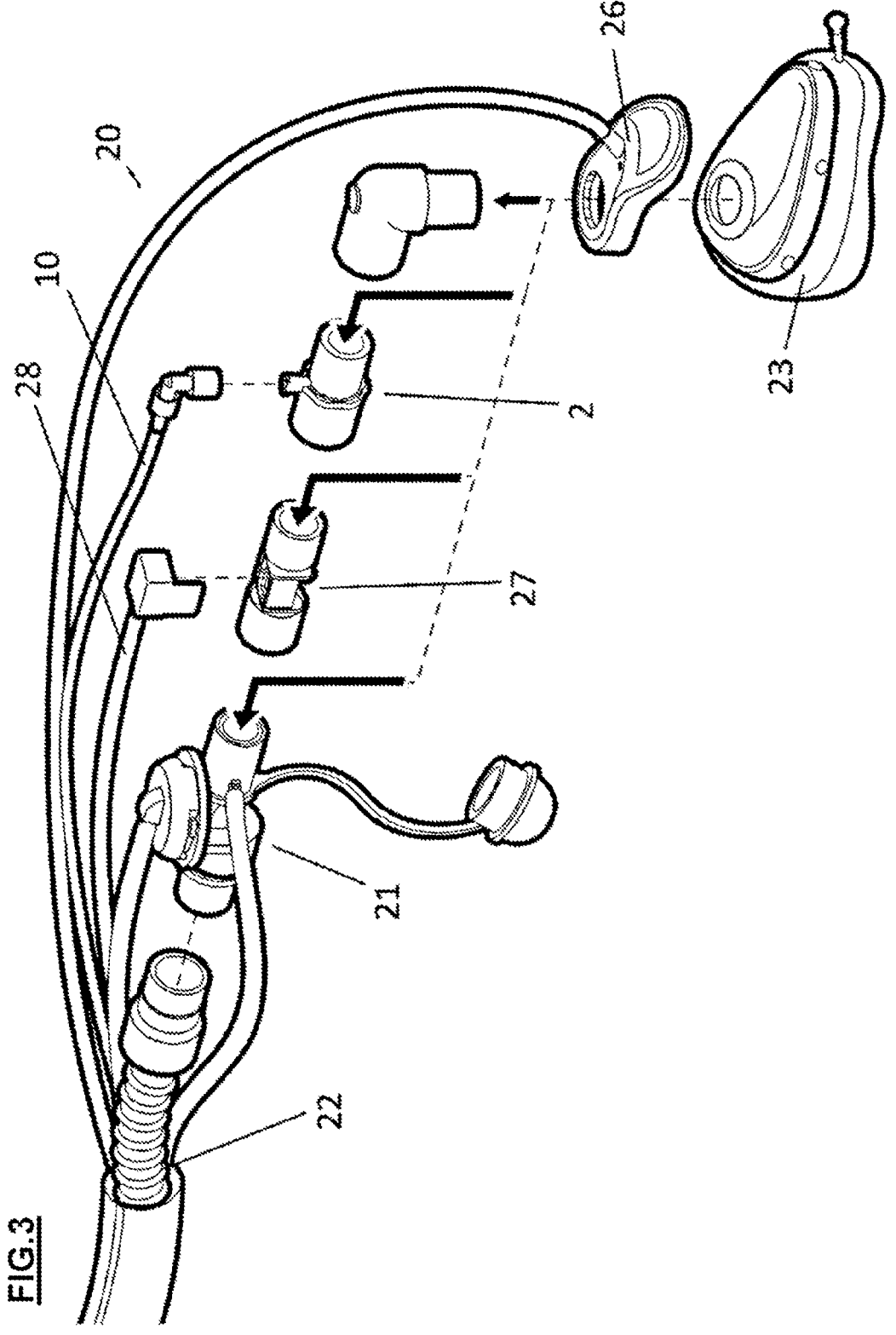
FIG. 3: shows a perspective view of an exploded drawing of part of a device for ventilation comprising a mechanism for collecting a gas sample from the respiratory air stream.

FIG. 3, which serves inter alia to illustrate the position of the connection device (2) in the system, depicts a perspective view of an exploded drawing of part of a device for ventilation (20) in the region of the patient valve (21), which device for ventilation (20) is according to the invention.

The patient valve (21) is connected to the respiratory air hose of the respiratory air line (22). The patient valve (21) comprises a check valve, a control line and a pressure measurement hose.

Following the patient valve (21) in the direction of the mask (23) is a flow sensor (27), which is connected via a connection line (28) to a control device or an evaluation unit (not depicted) of the device for ventilation (28).

Following the flow sensor (27) is the connection mechanism (2), which is connected to a withdrawal line (10). Conductable through the withdrawal line (10) are respiratory gas samples, from the region of the connection mechanism (2) toward the device for measuring the content of at least one gas in exhaled air (1), which device is not depicted here.

The connection mechanism (2) is connected via a 90° connection piece to the mask (23) and to a button (26) arranged on the mask (23), said button (26) being utilizable for triggering breaths of the device for ventilation (20). As an alternative to a button (26), embodiments of the invention can also comprise a remote control, by means of which the relevant function is controllable.

The depicted configuration of the patient hose system is designed as a one-hose system. As a deviation from this, the invention is also utilizable in two-hose systems, in which the respiratory gas is initially guided from the patient to the ventilator, where it is discharged via an exhaled air valve.

Figure 4:
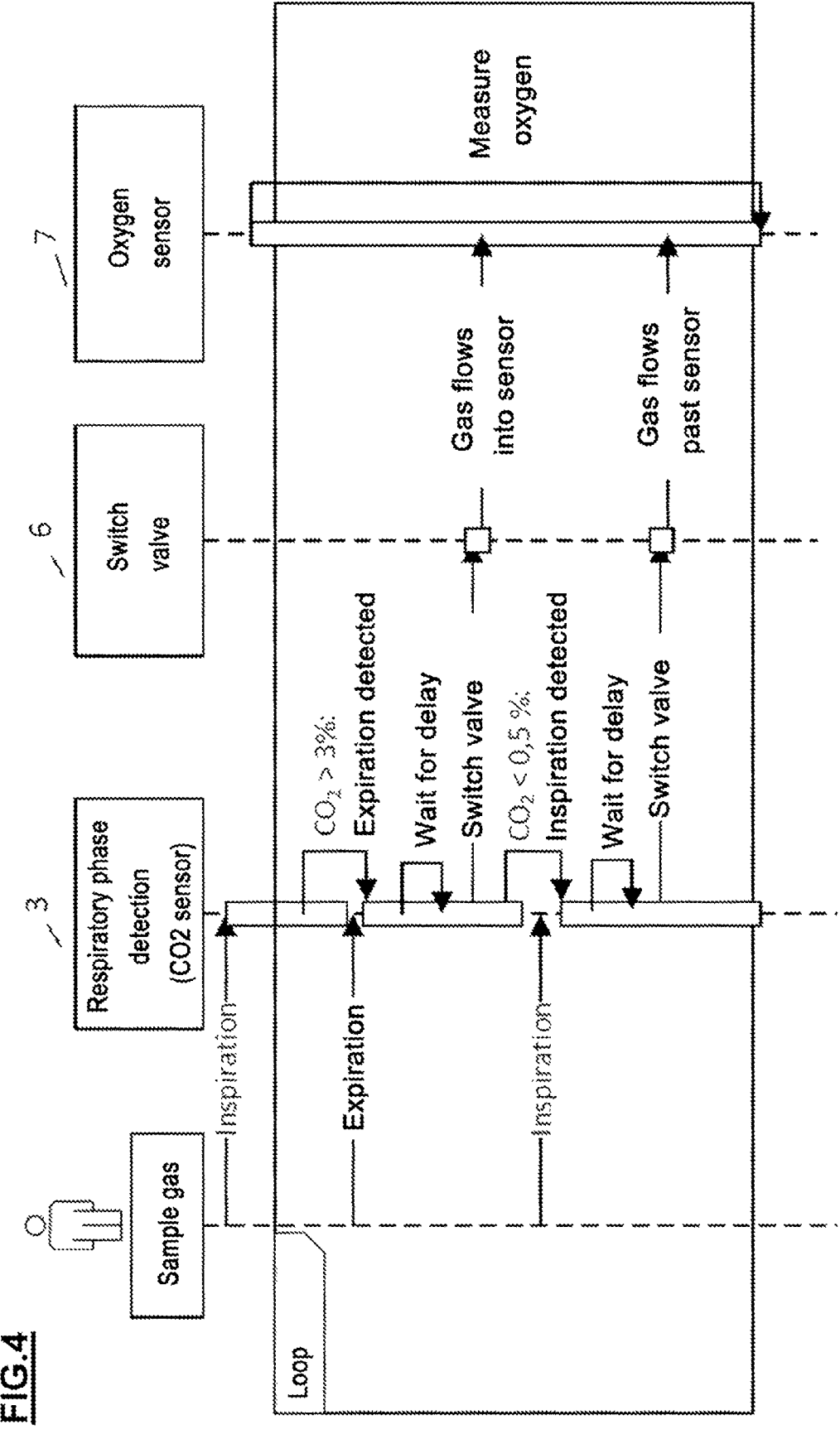
FIG. 4: shows a schematic flow chart of one embodiment of a method for measuring the content of at least one gas in exhaled air, which method is according to the invention.

FIG. 4 shows the sequence of one embodiment of the invention of a method for measuring the content of at least one gas in exhaled air.

With the aid of a device for determining the respiratory phase (3), the respiratory phase is detected on the basis of a sample gas withdrawn from the respiratory air of a patient. In the present exemplary embodiment, the CO2 content of the sample gas is determined with the aid of a respiratory phase sensor (9) designed as a CO2 sensor and threshold values are used to determine which respiratory phase is currently present. In this embodiment of the method, the first threshold value, which is used for detection of an expiration phase, is a CO2 content of 3% by volume, which must be exceeded.

Thereafter, a predefined period of time (delay) is waited for before the controllable valve (6) is switched. After the controllable valve (6) has been switched, the gas of the respiratory gas sample flows into the gas sensor (7), which is designed as an O2 sensor in this embodiment.

This is followed by measurement of the O2 content of the respiratory gas sample with the aid of the gas sensor (7). Meanwhile, respiratory phase detection continues without stopping, with an inspiration phase being detected through values below a second threshold value, which in this embodiment of the method is a CO2 content of 0.5% by volume, which must be fallen short of.

If an inspiration phase is detected, a defined period (delay) is waited for and the controllable valve (6) is then switched, so that the gas of the respiratory gas sample does not flow through the gas sensor (7) and flows past the gas sensor (7).

The abovementioned isolation phase is the period in which no new sample gas flows to the gas sensor (7), i.e., the period between the switching of the controllable valve (6) after the detection of an inspiration phase up to the switching of the controllable valve (6) after the detection of the subsequent expiration phase.

Figure 5:
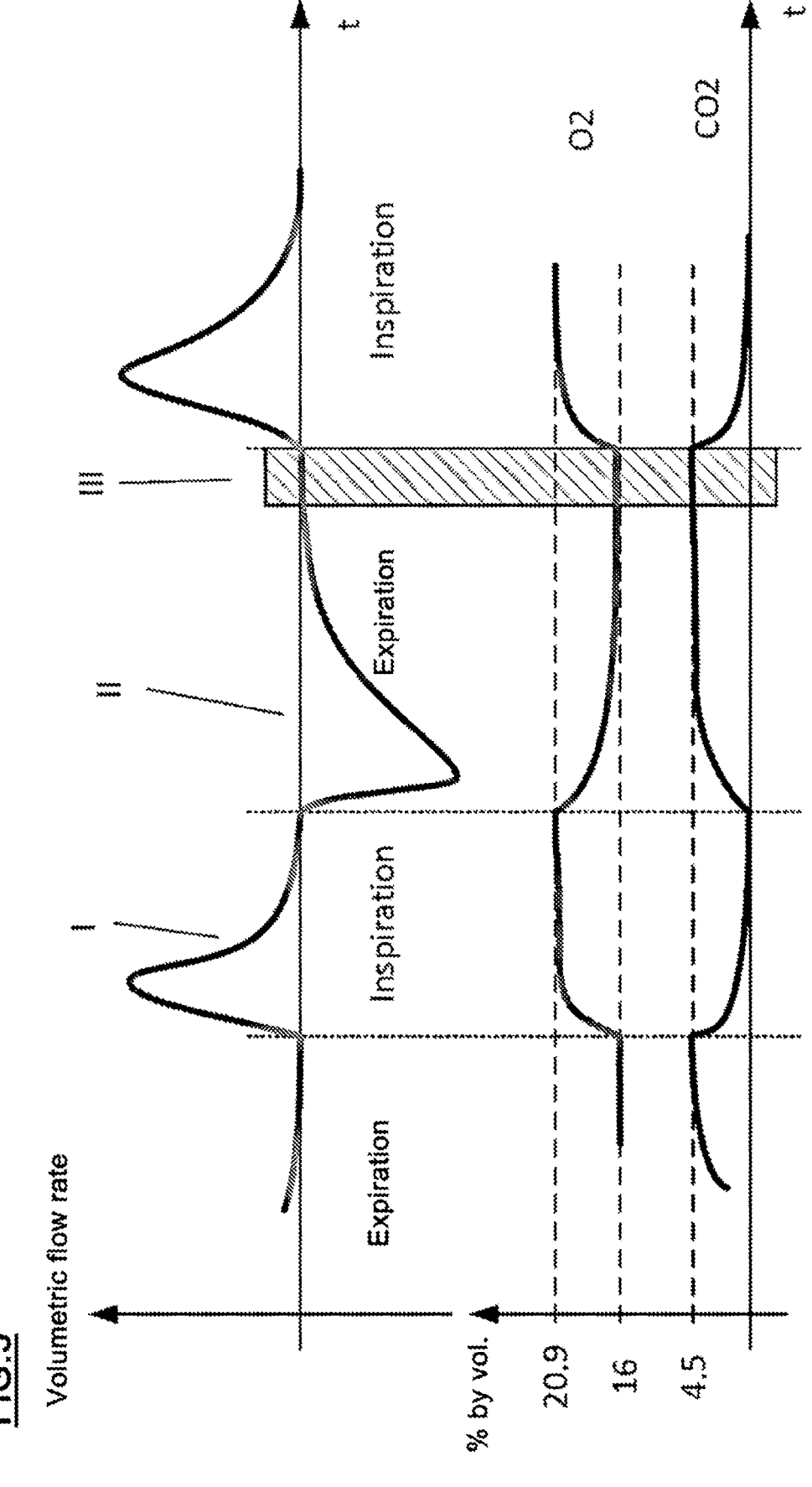
FIG. 5: shows a graph to illustrate the course of various measurement values over a respiratory cycle.

FIG. 5 depicts, in two connected graphs, the course of the flow of the respiratory air and of the CO2 content and O2 content of the respiratory air over one respiratory cycle. The abscissa (horizontal axis) is the time axis and the ordinate (vertical axis) is the volumetric flow rate [l/s] or the gas content [% by volume].

One respiratory cycle is divided into the phases inspiration phase (I) and expiration phase (II), the last segment of the expiration phase (II) being given by the end-tidal region (III).

During the inspiration phase, the volumetric flow rate of the respiratory gas first rises steeply and then falls again slowly. During the displacement of the exhaled air from the gas sensor, the O2 content of the respiratory gas sample rises from the end value of the preceding expiration phase (II) of about 16% by volume to the O2 content of the respiratory air source of the device for ventilation, in this case 20.9% by volume. In parallel, the CO2 content of the respiratory gas sample falls from the end value of the preceding expiration phase (II) of about 4.5% by volume to almost 0% by volume.

During the expiration phase (II), the volumetric flow rate first rises steeply in the opposite direction and then falls again slowly. During the displacement from the gas sensor of the respiratory air conducted toward the patient for ventilation, the O2 content of the respiratory gas sample falls from the end value of the preceding inspiration phase (I) of about 20.9% by volume to the O2 content of the exhaled air of the patient, in this case 16% by volume. In parallel, the CO2 content of the respiratory gas sample rises from the end value of the preceding inspiration phase (I) of almost 0% by volume to about 4.5% by volume.

In the end-tidal region (III), the values for the volumetric flow rate and for the O2 content and CO2 content only undergo very slight changes, and so it can be assumed that these measurement variables have virtually constant values in the end-tidal region. Regarding the O2 content and CO2 content, reference is made to the concentration plateaus already mentioned above.

The invention claimed is:

1. A device for measuring a content of at least one gas in exhaled air, comprising: at least one device for determining a respiratory phase; at least one control unit; at least one controllable multi-port valve, having at least one inlet and at least two outlets, and/or one pump device; and at least one gas sensor, wherein a current respiratory phase in a respiratory cycle is determinable by the device for determining the respiratory phase and the controllable valve and/or the pump device is actuable by the control unit according to the determined respiratory phase so that a respiratory gas sample of respiratory air that is flowing toward or away from a patient depending on the respiratory phase is passable through the gas sensor or isolatable in a region of the gas sensor, so that the content of the at least one gas in the exhaled air in a predetermined segment of the respiratory cycle is determined by the gas sensor, wherein the device for determining the respiratory phase has at least one respiratory phase sensor which configured as a fast sensor having a rise time of less than 500 ms, wherein the at least one gas sensor is an $O_2$ sensor configured as a slow sensor having a rise time of more than 500 ms for determining $O_2$ content in the respiratory gas sample, wherein the controllable multi-port valve is arranged downstream of the pump device and upstream of the gas sensor in a direction of flow of the respiratory gas sample, wherein the inlet of the multi-port valve is connected to the pump device, one of the outlets of the multi-port valve is connected to the gas sensor and another of the outlets of the multi-port valve is connected to an outlet, so that the respiratory gas sample is fed directly into the gas sensor or to the outlet depending on a valve position of the controllable multi-port valve.

2. The device according to claim 1, wherein the device for determining the respiratory phase is configured for main-stream measurement.

3. The device according to claim 1, wherein the device for determining the respiratory phase is configured for secondary-stream measurement.

4. The device according to claim 1, wherein the at least one respiratory phase sensor is a CO2 sensor, a temperature sensor, a humidity sensor, a flow sensor or a pressure sensor.

5. The device according to claim 1, wherein the controllable valve is a multiport valve comprising at least two input ports and at least two output ports, so that respiratory gas samples of various points of the system are passable through the gas sensor or isolatable in the region of the gas sensor according to the respiratory phase.

6. A device for ventilation, comprising at least one device for measuring a content of at least one gas in exhaled air according to claim 1.

7. A method for measuring a content of at least one gas in exhaled air using the device for measuring the content of at least one gas in exhaled air according to claim 1, comprising the steps of:
   a. determining a respiratory phase using the at least one respiratory phase sensor;
   b. detecting whether there is a predetermined respiratory phase in a respiratory cycle;
   c. supplying a gas sample to the at least one gas sensor;
   d. isolating the gas sample in a region of the at least one gas sensor;
   e. measuring the supplied gas sample with the aid of the at least one gas sensor; and
   f. terminating the isolation of the gas sample.

8. The method according to claim 7, including carrying out the determination of the respiratory phase and the detection of whether there is a predetermined respiratory phase continuously and in parallel to the other method steps.

9. The method according to claim 7, including carrying out the detection of the predetermined respiratory phase(s) based on specified threshold values for measurement values measured for determination of the respiratory phase, which measurement values must lie above or below the respective threshold values.

10. The method according to claim 7, including carrying out the respiratory phase with the device for determining the respiratory phase comprising the at least one respiratory phase sensor, wherein CO2 content, humidity, temperature, flow and/or pressure of respiratory air that is flowing toward or away from a patient is measured with the at least one respiratory phase sensor.

11. The method according to claim 7, including measuring an end-tidal oxygen content in exhaled air of a patient with the gas sensor.

* * * * *